(12) United States Patent
Reuter

(10) Patent No.: US 10,088,087 B2
(45) Date of Patent: Oct. 2, 2018

(54) CONNECTION SYSTEM

(71) Applicant: Marco Systemanalyse und Entwicklung GmbH, Dachau (DE)

(72) Inventor: Martin Reuter, Dachau (DE)

(73) Assignee: MARCO SYSTEMANALYSE UND ENTWICKLUNG GMBH, Dachau (DE)

( * ) Notice: Subject to any disclaimer, the term of this patent is extended or adjusted under 35 U.S.C. 154(b) by 0 days.

(21) Appl. No.: 15/498,568

(22) Filed: Apr. 27, 2017

(65) Prior Publication Data

US 2017/0227155 A1 Aug. 10, 2017

Related U.S. Application Data

(62) Division of application No. 14/613,848, filed on Feb. 4, 2015, now Pat. No. 9,683,683.

(30) Foreign Application Priority Data

Feb. 6, 2014 (DE) .......................... 10 2014 101 484

(51) Int. Cl.
| | |
|---|---|
| *F16L 37/252* | (2006.01) |
| *F16L 15/04* | (2006.01) |
| *F16L 15/08* | (2006.01) |
| *B65D 47/06* | (2006.01) |
| *A61M 39/10* | (2006.01) |
| *A61M 39/22* | (2006.01) |

(Continued)

(52) U.S. Cl.
CPC ........ *F16L 37/252* (2013.01); *A61M 39/1011* (2013.01); *A61M 39/22* (2013.01); *B65D 47/06* (2013.01); *F16L 15/04* (2013.01); *F16L 15/08* (2013.01); *A61M 2039/0036* (2013.01); *A61M 2039/1033* (2013.01); *A61M 2039/1094* (2013.01); *F16L 37/00* (2013.01)

(58) Field of Classification Search
CPC .......... B65D 47/06; F16L 15/04; F16L 15/08; F16L 37/252; F16L 37/00; A61M 2039/0036; A61M 2039/1033; A61M 2039/1094; A61M 39/1011; A61M 39/22
See application file for complete search history.

(56) References Cited

U.S. PATENT DOCUMENTS

| | | |
|---|---|---|
| 4,076,285 A | 2/1978 | Martinez |
| 4,439,188 A | 3/1984 | Dennehey et al. |
| 4,643,467 A | 2/1987 | Wood |

(Continued)

FOREIGN PATENT DOCUMENTS

| | | |
|---|---|---|
| CN | 1655876 A | 8/2005 |
| DE | 2634637 A1 | 2/1978 |

(Continued)

*Primary Examiner* — Frederick C Nicolas
(74) *Attorney, Agent, or Firm* — Cantor Colburn LLP

(57) ABSTRACT

The invention relates to a connection system having a first connection part which defines a first passage and to a second connection part to be connected to the first connection part which defines a second passage which is orientated with the first passage in the connected state of the connection parts, wherein the first connection part has a blunt cone section through which the first passage extends and the second connection part has a reception section having a frustoconical reception space for receiving the blunt cone section into which the second passage opens.

8 Claims, 3 Drawing Sheets

Figure 1A:
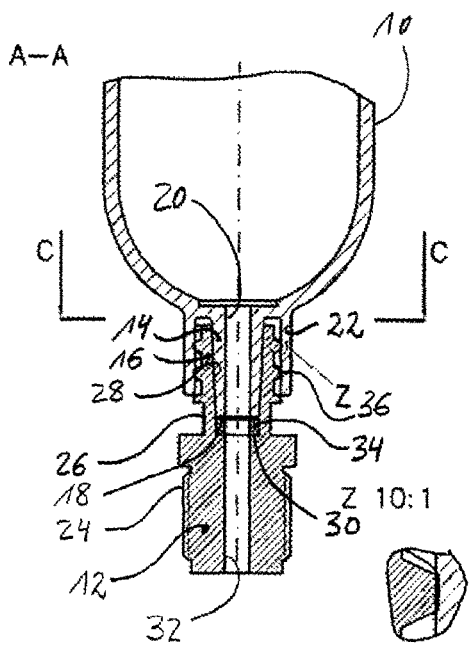

(51) Int. Cl.
*A61M 39/00* (2006.01)
*F16L 37/00* (2006.01)

(56) References Cited

U.S. PATENT DOCUMENTS

| | | | |
|---|---|---|---|
| 6,261,282 B1 | 7/2001 | Jepson et al. | |
| 6,684,918 B1 | 2/2004 | Thilly et al. | |
| 7,025,744 B2 | 4/2006 | Utterberg et al. | |
| 7,056,308 B2 | 6/2006 | Utterberg | |
| 7,708,714 B2 * | 5/2010 | Connell | A61M 1/285 604/30 |
| 7,803,139 B2 | 9/2010 | Fangrow, Jr. | |
| 7,824,393 B2 | 11/2010 | Fangrow | |
| 8,777,931 B2 | 7/2014 | Davis et al. | |
| 9,683,683 B2 * | 6/2017 | Reuter | B65D 47/06 |
| 2004/0139626 A1 | 7/2004 | Cote, Sr. | |

FOREIGN PATENT DOCUMENTS

| | | |
|---|---|---|
| EP | 1508380 A1 | 2/2005 |
| JP | S63218328 A | 9/1988 |
| KR | 1020000069023 | 11/2000 |
| KR | 1020010106531 | 12/2001 |

\* cited by examiner

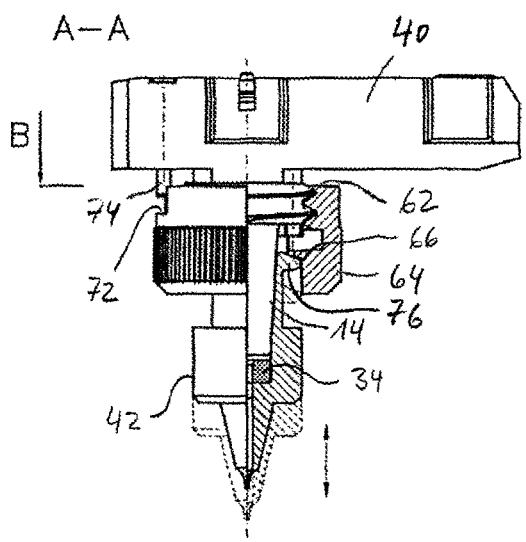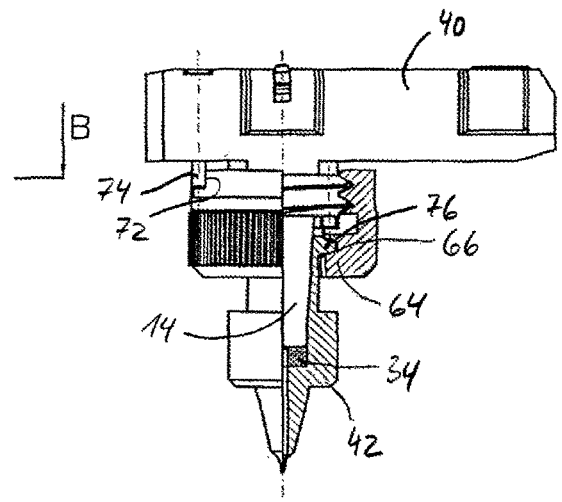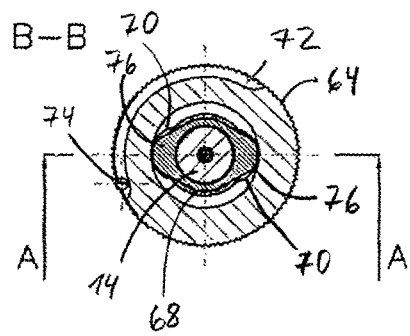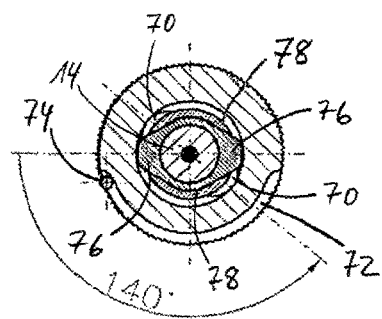

CONNECTION SYSTEM

This patent application is a divisional application of U.S. patent application Ser. No. 14/613,848 filed on Feb. 4, 2015, which claims priority to German Patent Application No. DE102014101484.7, filed Feb. 6, 2014, which both incorporated herein by reference in its entirety.

The invention relates to a connection system having a first connection part which defines a first passage and to a second connection part to be connected to said first connection part which defines a second passage which is orientated with the first passage in the connected state of the connection parts, wherein the first connection part has a blunt cone section through which the first passage extends and the second connection part has a reception section having a frustoconical reception space for receiving the cone section into which the second passage opens.

Such a connection system is known, for example, from medical engineering under the name Luer system or Luer lock system and is used there e.g. to fasten cannulas to syringes. In accordance with existing standards, the jacket surface of the cone section of a Luer system has a 6% taper and the taper of the wall surface of the reception section defining the reception space is adapted to the taper of the jacket surface of the cone section such that the cone section comes into friction-locking and sealing engagement with the reception section on the introduction into the reception space.

To ensure a sufficient leak tightness and a sufficient adhesion of the cone section in the reception section, there must always be a spacing between the top face of the cone section and the opening aperture of the second passage in this respect due to production tolerances, said opening aperture typically having a smaller cross-section than the reception space. This spacing between the cone section and the opening aperture of the second passage forms a so-called "dead space", i.e. a volume which is not continuously flushed through. This dead space makes a use of conventional Luer systems impossible in metering technology since it is here ultimately not important that the passage cross-section is also as constant as possible at the connection points between components to be connected, e.g. between a fluid reservoir and a metering nozzle or between a fluid reservoir and a metering valve or between a metering valve and a metering nozzle.

It is an object of the invention to provide a connection system in the manner of a Luer system which can also be used in metering technology.

The object is satisfied by a connection system having the features of claim 1 and in particular in that the cone section (i.e. a section of the first connection part that is formed as a truncated cone) seals at the front face toward a planar base of the reception space in the connected state of the connection parts.

It is the principle underlying idea of the invention not to implement the seal between the first connection part and the second connection part as customary with conventional Luer systems via the jacket surface of the cone section, but rather via the end face or top face of the cone section. Unlike with conventional Luer systems, it is therefore not necessary in accordance with the invention that the jacket surface of the cone section is in friction-locking and sealing engagement with the reception section. A specific clearance is rather provided between the cone section and the reception section which allows the cone section to be introduced so far into the reception space that the top face of the cone section directly or indirectly abuts the base of the reception space. A dead space between the cone section and the opening aperture of the second passage is thereby avoided and a transition from the first passage to the second passage can be achieved with a minimal cross-sectional change so that the connection system in accordance with the invention is also suitable for use in metering technology.

In principle, only the cone diameter of one of the two connection parts has to be modified with respect to conventional Luer systems for the implementation of a connection system in accordance with the invention. It is, for example, sufficient if the reception space of the second connection part is somewhat wider than the standards defining Luer systems provide. It is generally possible in this manner to use standard components confirming to the standards for the respective other connection part, whereby the connection system in accordance with the invention can be produced particularly economically.

Advantageous embodiments of the invention can be seen from the dependent claims, from the description and from the drawing.

In accordance with an embodiment, the cone section can be introduced so far into the reception space that the top face of the cone section sealingly contacts the base of the reception space in the connected state of the connection parts. It is, however, alternatively also possible to arrange a sealing element between the top face of the cone section and the base, in particular a sealing ring, e.g. composed of Teflon or of a similar material.

Since the jacket surfaces of the cone section and the reception section are not in friction-locking and sealing engagement with one another in accordance with the invention, unlike with conventional Luer systems, the connection system advantageously comprises separate securing means which secure the connection parts to one another in the connected state.

For example, the cone section can be at least partly surrounded by a sleeve, e.g. a threaded sleeve, and the reception section can be provided at its outer side with a thread which is in friction-locking engagement with an inner surface of the sleeve in the connected state of the connection parts such that an independent release of the second connection part from the first connection part is precluded. In this respect, a maximum outer diameter of the thread is larger than an inner diameter of the sleeve and the thread is provided at the outer side with a plurality of planar faces arranged distributed over the periphery, that is it is provided so-to-say with a facet cut.

In accordance with an alternative embodiment, the jacket surface of the cone section is provided at least regionally with an external thread with which a securing nut is in engagement to secure the second connection part to the first connection part.

Limiting means are advantageously provided which limit a rotation of the securing nut relative to the cone section to an angular range of less than 180°, e.g. 20° to 160°, in particular 24°, to prevent any unintended release of the securing nut from the cone section and to hold the securing nut in a desired axial position. The limiting means can, for example, comprise a limiting pin fixedly connected to a base of the cone section and a cut-out of the securing nut which extends along the periphery of the securing nut over the named angular range and into which the limiting pin engages.

The reception section can have at least one radially protruding projection or vane in the region of its end facing the first connection part to couple the second connection part to the securing nut, while the securing nut is provided at its inner side with a peripheral groove with which the at least one projection can be brought into engagement. Two projections or vanes projecting radially in opposite directions are preferably provided at the reception section for a better force absorption. These two projections, together with the limited rotatability of the securing nut by less than 180°, furthermore provides that the second connection part cannot accidentally fall out of the securing nut on a rotation of the securing nut after being plugged onto the cone section and being inserted into the securing nut.

For an additional securing of the second connection part to the first connection part, blocking means can moreover be provided which prevent an unintended rotation of the reception section relative to the cone section in the connected state of the connection piece.

A further subject of the invention is additionally a metering apparatus having e container containing fluid to be metered, a metering nozzle, e.g. a metering needle, and a metering valve connected between the container and the metering nozzle, wherein the container and the metering valve and/or the metering valve and the metering nozzle are each connected to one another by a connection system in accordance with the invention.

In this respect, it is not necessary for the container and the metering valve to be directly connected to one another. Depending on the application, a connection piece, e.g. in the form of an angle piece, can, for example, be connected between the container and the metering valve which is in turn connected to the container by means of a connection system in accordance with the invention. It is understood that an intermediate piece can generally also be connected between the metering valve and the metering nozzle and can be connected to the one and/or the other connection part by means of a connection system in accordance with the invention.

Figure 1B:
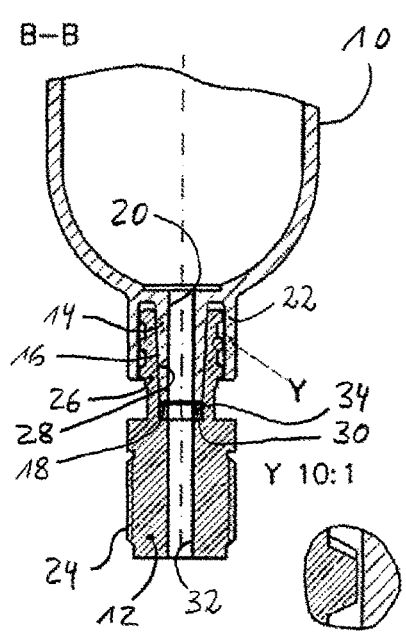
Figure 1C:
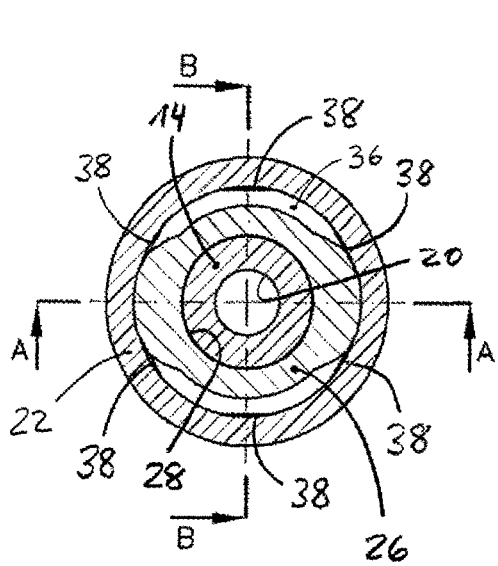
Figure 1D:
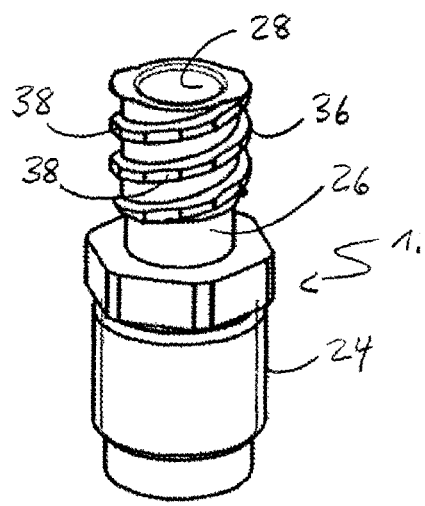
Figure 2:
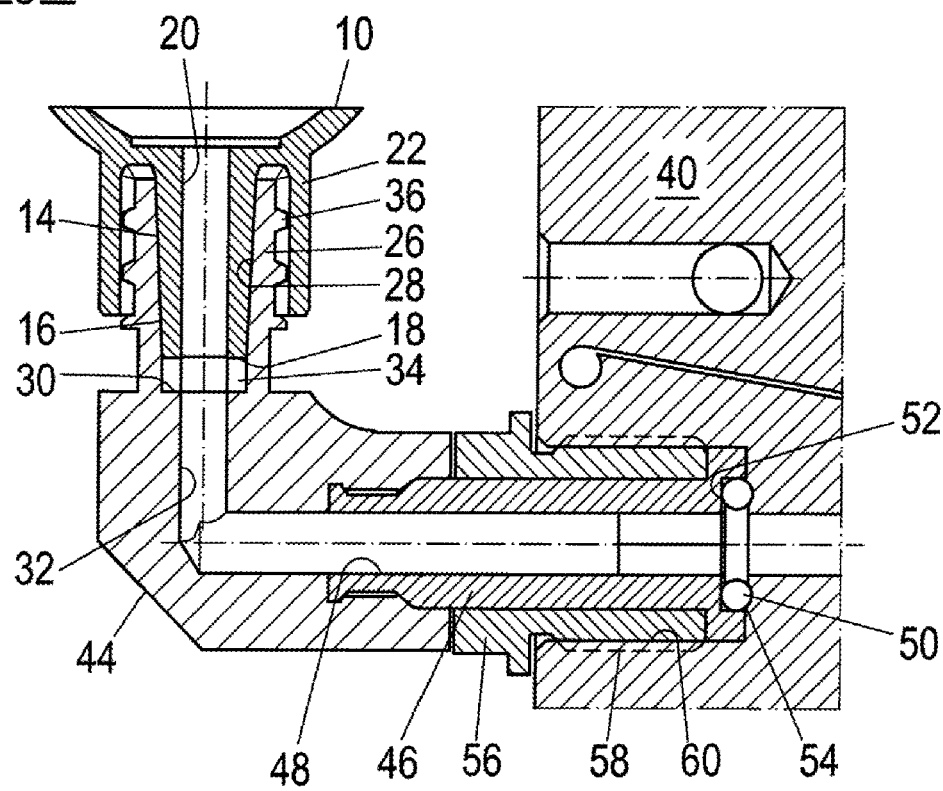
Figure 3:
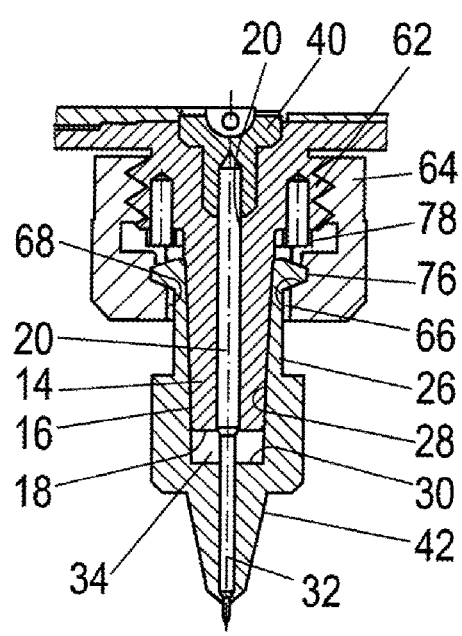

The invention will be described in the following with reference to possible embodiments and to the enclosed drawing. There are shown:

FIGS. 1A-C different sectional views of a first embodiment of a connection system in accordance with the invention with a first connection part and a second connection part;

FIG. 1D a perspective view of the second connection part;

FIG. 2 a sectional view of a container, of an angle piece and of the inlet side of a metering valve of a metering apparatus in accordance with the invention;

FIG. 3 a sectional view of a second embodiment of a connection system in accordance with the invention for attaching a metering nozzle to the outlet side of the metering valve of FIG. 2;

FIGS. 4A and B partly longitudinally sectioned view of the connection system of FIG. 3; and FIGS. 4C and D cross-sectional view of the connection system of FIG. 3.

A connection system for connecting a container 10 (first connection part) containing a fluid to a connection piece 12 (second connection part) is shown in FIG. 1. In the present embodiment, the container 10 is an injection molded plastic part, specifically a cartridge manufactured from a plastic material. The connection piece 12 can in turn be formed from a plastic material or alternatively from a metal material.

A blunt cone section 14, i.e. a section having the shape of a truncated cone, having a jacket surface 16 and a top face 18 is molded to the container 10. The taper of the jacket surface 16 of the cone section 14 amounts to 6% with respect to the axis of symmetry of the cone section 14 which is used as a reference axis for the terms "axial" and "radial". A first axial passage 20 extends through the cone section 14; its one end opens into the interior of the container 10 and its other end is open at the top face 18. The cone section 14 is surrounded over a large part of its height by a cylindrical sleeve 22, here a threaded sleeve, which is molded to the container 10 and which is orientated coaxially with the cone section 14.

The connection piece 12 comprises a main section 24 and a reception section 26 which adjoins it and which defines a reception space 28 for receiving the cone section 14. The reception space 28 is in turn of conical shape and forms a blunt internal cone whose top face is defined by a planar base 30 at the transition between the reception section 26 and the main section 24.

A second axial passage 32 which opens into the reception space 28 at the base 30 and whose cross-section is at least approximately the same as the cross-section of the first axial passage 20 extends through the main section 24.

A sealing element 34 which surrounds the opening aperture of the second axial passage 32 is fitted into the reception space 28 at the base 30, in the present embodiment a seal composed of Teflon. The inner cross-section of the sealing element 34 is adapted to the cross-sections of the first axial passage 20 and of the second axial passage 32.

The reception space 28 is somewhat wider than the cone section 14 so that the cone section 14 can be introduced so far into the reception section 26 that the top face 18 of the cone section 14 abuts the sealing element 34 and provides a seal toward it in the connected state of the connection parts.

As FIGS. 1A and 1B show, a part of the reception section 26 is received in the ring gap between the cone section 14 and the sleeve 22 in the connected state of the connection parts. To prevent an unintended solution of the connection piece 12 from the container 10, the reception section 26 has an external thread 36 at its outer side whose maximum outer diameter is somewhat larger than the inner diameter of the sleeve 22. To screw the container 10 to the connection piece 12 (or vice versa), a specific frictional force therefore has to be overcome between the sleeve 22 and the external thread 36 which provides that the container 10 cannot rotate independently relative to the connection piece 12 and be released therefrom under normal circumstances.

The screwing of the reception section 26 into the sleeve 22 is accompanied by a deformation of the sleeve 22 formed from plastic material due to the larger external thread 36. To prevent any damage to the sleeve 22, in particular a tearing of the sleeve 22, the external thread 36 is provided with a plurality of planar faces 38 which are arranged distributed along the periphery and which reduce the deformation of the sleeve 20 from a continuous deformation to a cyclic deformation. In the present embodiment, six such planar faces 38 are provided over 360°; however, other divisions are also possible, for example two to ten planar faces.

FIG. 2 shows the use of the above-described connection system in a metering apparatus which serves to output a fluid contained in a container 10 via a metering valve 40 and a metering nozzle 42 (FIGS. 3 and 4) in a controlled manner.

The container 10 is connected to an input of the metering valve 40 via an angle piece 44. At the container side, the angle piece 44 is formed like the connection piece 12 and is connected to the container 10 in the manner described with reference to FIG. 1.

In contrast to the connection piece of FIG. 1, the angle piece 44, however, deflects the second passage 20 extending therein by 90° to allow a lateral attachment of the container 10 to the metering valve 40 with a simultaneously perpendicular arrangement of the container 10.

At the valve side, a tube piece 45 is fixedly joined to the angle piece 44, e.g. by means of a threaded connection, a bonded connection and/or a press connection. The tube piece 46 has a third passage 48 which communicates with the second passage 32 of the angle piece 44 and which is open at the end face of the tube piece 46 at the valve side. The opening aperture of the third passage 48 is surrounded by a sealing ring 50 which is inserted into a ring-shaped cut-out 52 in the end face of the tube piece 46 and which is held therein by a holding claw 54.

The tube piece 46 is surrounded by a threaded sleeve 56 which is freely rotatable with respect to the tube piece 46 and which is prevented from an axial movement by shoulders of the angle piece 44 and of the tube piece 46. The threaded sleeve 56 has an external thread and is screwed into a corresponding threaded bore 60 of the metering valve 40 for mounting the angle piece 44 to the metering valve 40. A desired orientation of the container 10 can be set or maintained when screwing the threaded sleeve 56 into the threaded bore 60 thanks to the rotatability of the threaded sleeve 56 relative to the tube piece 46. The container 10 can be fixed in the desired orientation by tightening the threaded sleeve 56 in the threaded bore 60.

The attachment of the metering nozzle 42, here in the form of a metering needle, at the outlet of the metering valve 40 takes place by means of a second embodiment of the connection system which is shown in FIGS. 3 and 4.

A blunt cone section 14 having a jacket surface 16 and a top face 18 forms the outlet of the metering valve 40 (first connection part). A first axial passage 20 which is open toward the top face 18 extends coaxially to the axis of symmetry of the cone section 14 in the interior of the cone section 14. The jacket surface 16 has a taper of 6% with respect to the axis of symmetry.

In the region of its base, the cone section 14 is provided with an external thread 62 onto which a securing nut 64 is screwed. The taper of the external thread 62 is selected so small that the securing nut 64 is self-locking.

The securing nut 64 has a section which projects axially beyond the external thread 62 and at whose inner side a peripheral groove 66 is formed. At the end face, the projecting section of the securing nut 64 has a bore 68 through which the cone section 14 extends and which has two mutually oppositely disposed radial indentations 70 which extend up to and into the peripheral groove 66 in the axial direction.

To restrict a rotation of the securing nut 64 relative to the cone section 14, a cut-out 72 is introduced into the end face of the securing nut 64 which faces toward the metering valve 40 and which extends over an angular range of 140° in the peripheral direction. A limiting pin 74 attached to the metering valve 40 engages into the cut-out 72 and thus prevents the securing nut 64 from being rotated by more than 140°.

The metering nozzle 42 (second connection part) to be connected to the metering valve 40 comprises a reception section 26, which defines a frustoconical reception space 28, and a main section 24 which adjoins it and in which a second axial passage 32 extends which opens into the reception space 28 at a planar base 30 thereof. A sealing element 34, e.g. a sealing ring of Teflon or of a similar material, is fitted into the reception space 28 at the base of the reception space 28 which surrounds the opening aperture of the second axial passage 32.

In the region of the end of the metering nozzle 42 facing the metering valve 40, two projections 76 or vanes project from the reception section 26; they extend in opposite directions radially and their contour is matched to the indentations 70 of the securing nut 64.

In a similar manner as in the first embodiment, the reception space 28 is somewhat larger than the cone section 14 so that the cone section 14 can be introduced so far into the reception space 28 that it abuts the sealing element 34 at the end face and provides a seal toward it.

The securing nut 64 must be in its released rotational position (FIG. 4A) for the mounting of the metering nozzle 42 to the metering valve 40. The radial projections 76 of the metering nozzle 42 must furthermore be orientated with the indentations 70 of the securing nut 64 so that the reception section 26 can move axially into the securing nut 64 to bring the cone section 14 into contact with the sealing element 34. The contact between the cone section 14 and the sealing element 34 ideally takes place approximately when the radial projections 76 are at the level of the peripheral groove 66 of the securing nut 64.

While rotating the securing nut 64 about the named 140° relative to the cone section 14, the securing nut 64 is subsequently tightened to pull the metering nozzle 42 even further in the direction of the metering valve 40 and to compress the sealing element 34 by a maximum between the cone section 14 and the base 30 (FIG. 4B) to achieve an ideal sealing effect.

In addition, the radial projections 76 of the metering nozzle 42 are brought into engagement with the peripheral groove 66 of the securing nut 64 by the rotation of the securing nut 64 and the indentations 70 of the securing nut 64 and the radial projections 76 are simultaneously brought out of coverage, whereby the metering nozzle 42 is now secured against falling out of the securing nut 64.

A rotation of the metering nozzle 42 relative to the cone section 14 is in this respect prevented by two blocking walls 78 which are of part-ring shape and which project axially so far from the external thread 62 of the cone section 14 on oppositely disposed sides of the cone section 14 that they end approximately at the level of the radial projections 76 with a metering nozzle 42 plugged on. Viewed in the peripheral direction, the blocking walls 78 define two oppositely disposed blocking receivers which are orientated with the indentations 70 of the securing nut 64 and with the radial projections 76 on the plugging on of the metering nozzle 42 so that the radial projections 76 can move into the blocking receivers. When tightening the securing nut 64, the radial projections 76 are seated tight in the blocking receivers and cannot rotate with the securing nut 64. The radial projections 76 can consequently not orientate themselves independently with the indentations 70, whereby an unintended release of the metering nozzle 42 from the metering valve 40 is precluded.

REFERENCE NUMERAL LIST 10 container
12 connection piece
14 cone section
16 jacket surface
18 top face
20 passage
22 sleeve
24 main section
26 reception section
28 reception space 30 base surface
32 passage
34 sealing element
36 external thread
38 planar face
40 metering valve
42 metering nozzle
44 angle piece
46 tube piece
48 passage
50 sealing ring
52 cut-out
54 holding claw
56 threaded sleeve
58 external thread
60 threaded bore
62 external thread
64 securing nut
66 groove
68 bore
70 indentation
72 cut-out
74 limiting pin
76 projection
78 blocking wall

The invention claimed is:

1. A connection system having a first connection part which defines a first passage and having a second connection part which is to be connected thereto and which defines a second passage, the second passage being orientated with the first passage in a connected state of the connection parts, wherein the first connection part has a blunt cone section through which the first passage extends and the second connection part has a reception section having a frustoconical reception space for receiving the blunt cone section into which the second passage opens,
wherein the blunt cone section seals toward a planar base of the reception space at an end face in the connected state of the connection parts, and
wherein a jacket surface of the blunt cone section is at least regionally provided with an external thread and a securing nut provided for securing the second connection part to the first connection part is in engagement with the external thread.

2. The connection system in accordance with claim 1, further comprising limiting means which limit a rotation of the securing nut relative to the blunt cone section to an angular range of less than 180°.

3. The connection system in accordance with claim 2, in which the limiting means comprise a limiting pin fixedly connected to a base of the blunt cone section and a cut-out of the securing nut which extends along the periphery of the securing nut over the angular region and into which the limiting pin engages.

4. The connection system in accordance with claim 1, in which the reception section has at least one radially protruding projection in a region of an end of the reception section facing the first connection part and the securing nut is provided at the inner side with a peripheral groove with which the at least one projection can be brought into engagement.

5. The connection system in accordance with claim 1, further comprising blocking means which block a rotation of the reception section relative to the blunt cone section in the connected state of the first and second connection parts.

6. The connection system in accordance with claim 1, in which the blunt cone section can be introduced so far into the reception space that a top face of the blunt cone section sealingly contacts a base of the reception space in the connected state of the connection parts.

7. The connection system in accordance with claim 1, further comprising a sealing element that is arranged between a top face of the blunt cone section and a base.

8. A metering apparatus having a container containing a fluid to be metered, a metering nozzle and a metering valve connected between the container and the metering nozzle, wherein the container and the metering valve and/or the metering valve and the metering nozzle are each connected to one another by a connection system in accordance with claim 1.

* * * * *